(12) United States Patent
Fenton et al.

(10) Patent No.: US 10,434,526 B2
(45) Date of Patent: Oct. 8, 2019

(54) MIST GENERATING APPARATUS

(71) Applicant: Tyco Fire & Security GmbH, Neuhausen am Rheinfall (CH)

(72) Inventors: Marcus Brian Mayhall Fenton, St. Neots (GB); Paul Stuart Hutcheson, Guildford (GB); James French, Huntingdon (GB); Jude Alexander Glynn Worthy, Huntingdon (GB)

(73) Assignee: 3M Innovative Properties Company, St. Paul, MN (US)

( * ) Notice: Subject to any disclaimer, the term of this patent is extended or adjusted under 35 U.S.C. 154(b) by 720 days.

(21) Appl. No.: 14/550,573

(22) Filed: Nov. 21, 2014

(65) Prior Publication Data
US 2015/0076243 A1 Mar. 19, 2015

Related U.S. Application Data

(63) Continuation of application No. 14/342,777, filed as application No. PCT/GB2012/052108 on Aug. 28, 2012, now abandoned.

(30) Foreign Application Priority Data

Sep. 7, 2011 (GB) .................................. 1115412.7

(51) Int. Cl.
*B05B 1/02* (2006.01)
*B05B 7/04* (2006.01)
(Continued)

(52) U.S. Cl.
CPC ............... *B05B 7/0483* (2013.01); *A61L 9/14* (2013.01); *A62C 31/03* (2013.01); *A62C 99/0072* (2013.01); *F24F 6/12* (2013.01)

(58) Field of Classification Search
CPC ....... B05B 7/0483; B05B 7/04; B05B 7/0466; B05B 7/0416; B05B 7/0807; B05B 7/0815; F24F 6/12; A62C 99/0072; A61L 9/14
(Continued)

(56) References Cited

U.S. PATENT DOCUMENTS 4,655,395 A * 4/1987 Cioffi ...................... B05B 1/265
239/427
5,333,794 A * 8/1994 Haruch ...................... B05B 1/00
239/523

(Continued)

FOREIGN PATENT DOCUMENTS

CN 201366386 12/2009
DE 20118801 6/2002

OTHER PUBLICATIONS

IFW, European Patent Application No. 12768885, Sep. 25, 2017, 114 pages.
(Continued)

*Primary Examiner* — Steven J Ganey
*Assistant Examiner* — Tuongminh N Pham (57) ABSTRACT

An improved mist generating apparatus is provided, the apparatus having a longitudinal axis (L), and first and second opposing nozzle surfaces (100,102) which define a nozzle between them. A first process fluid passage (28) has an inlet connectable to a supply of process fluid, and a process fluid outlet (110) on one or the first and second nozzle surfaces (100,102) such that the process fluid outlet (110) opens into the nozzle. The nozzle has a nozzle inlet (104) connectable to a supply of driving fluid, a nozzle outlet (108), and a throat portion (106) intermediate the nozzle inlet (104) and nozzle outlet (108). The nozzle throat (106) has a cross sectional area which is less than that of both the nozzle inlet (104) and the nozzle outlet (108). The nozzle extends
(Continued)

radially away from the longitudinal axis (L) such that the nozzle defines a rotational angle about the longitudinal axis (L). A centre line (CL) of the nozzle extends from the nozzle throat (106) to the nozzle outlet (108) at an angle of between 50 and 80 degrees relative to the longitudinal axis (L).

13 Claims, 8 Drawing Sheets

(51) Int. Cl.
    *A62C 31/03*     (2006.01)
    *A62C 99/00*     (2010.01)
    *A61L 9/14*     (2006.01)
    *F24F 6/12*     (2006.01)

(58) Field of Classification Search
    USPC .............................. 239/428, 433, 434.5, 601
    See application file for complete search history.

(56) References Cited

U.S. PATENT DOCUMENTS

| | | | |
|---|---|---|---|
| 6,039,269 | A | 3/2000 | Mandzukic |
| 6,322,003 | B1 * | 11/2001 | Haruch ................. B05B 7/0458 |
| | | | 239/290 |
| 8,789,769 | B2 | 7/2014 | Fenton et al. |
| 8,991,727 | B2 | 3/2015 | Worthy et al. |
| 9,004,375 | B2 | 4/2015 | Fenton et al. |
| 9,010,663 | B2 | 4/2015 | Fenton et al. |
| 9,050,481 | B2 | 6/2015 | Fenton et al. |
| 9,089,724 | B2 | 7/2015 | Fenton et al. |
| 9,216,429 | B2 | 12/2015 | Worthy et al. |
| 9,498,787 | B2 | 11/2016 | Fenton et al. |
| 2002/0125015 | A1 | 9/2002 | Crabtree |
| 2009/0314500 | A1 * | 12/2009 | Fenton ................... A62C 31/02 |
| | | | 169/16 |
| 2010/0230119 | A1 * | 9/2010 | Worthy ................. A62C 31/02 |
| | | | 169/46 |
| 2013/0228348 | A1 | 9/2013 | Worthy |
| 2014/0076996 | A1 | 3/2014 | Hayton |
| 2014/0246509 | A1 | 9/2014 | Fenton et al. |
| 2015/0048176 | A1 | 2/2015 | Jones et al. |
| 2015/0202639 | A1 | 7/2015 | Fenton et al. |
| 2015/0202640 | A1 | 7/2015 | Fenton et al. |
| 2016/0030899 | A1 | 2/2016 | Worthy et al. |
| 2016/0030958 | A1 | 2/2016 | Dyer et al. |
| 2016/0038954 | A1 | 2/2016 | Fenton et al. |
| 2016/0136672 | A1 | 5/2016 | Doswell |

OTHER PUBLICATIONS

International Search Report and Written Opinion, International Application No. PCT/GB2012/052108, dated May 12, 2012, 8 pages.
U.S. Appl. No. 12/381,584 (Publication No. 2009-0314500 A1) Now U.S. Pat. No. 8,789,769 issued Jul. 29, 2014; Related Application to U.S. Appl. No. 14/550,573.
U.S. Appl. No. 12/996,348 (Publication No. 2011-0127347 A1) Now U.S. Pat. No. 8,991,727 issued Mar. 31, 2015; Related Application to U.S. Appl. No. 14/550,573.
U.S. Appl. No. 12/742,046 (Publication No. 2011 0203813 A1) Now U.S. Pat. No. 9,498,787 issued Nov. 22, 2016; Related Application to U.S. Appl. No. 14/550,573.
U.S. Appl. No. 12/592,930 (Publication No. 2010-0230119 A1) Now U.S. Pat. No. 9,216,429 issued Dec. 22, 2015; Related Application to U.S. Appl. No. 14/550,573.
U.S. Appl. No. 12/741,941 (Publication No. 2010-0301129 A1) Now U.S. Pat. No. 9,050,481 issued Jun. 9, 2015; Related Application to U.S. Appl. No. 14/550,573.
U.S. Appl. No. 10/590,527 (Publication No. 2008-0230632 A1) Now U.S. Pat. No. 9,004,375 issued Apr. 14, 2015; Related Application to U.S. Appl. No. 14/550,573.
U.S. Appl. No. 14/672,015 (Publication No. 2015-0202639 A1) Co-Pending Related Application to U.S. Appl. No. 14/550,573.
U.S. Appl. No. 14/672,052 (Publication No. 2015-0202640 A1) Co-Pending Related Application to U.S. Appl. No. 14/550,573.
U.S. Appl. No. 14/274,311 (Publication No. 2014-0246509 A1) Co-Pending Related Application to U.S. Appl. No. 14/550,573.
U.S. Appl. No. 14/638,912 (Publication No. 2016-0030899 A1) Co-Pending Related Application to U.S. Appl. No. 14/550,573.
U.S. Appl. No. 13/862,101 (Publication No. 2013-0228348 A1) Related Application to U.S. Appl. No. 14/550,573.
U.S. Appl. No. 10/590,456 (Publication No. US 2007-0210186 A1) Now U.S. Pat. No. 9,010,663 issued Apr. 21, 2015; Related Application to U.S. Appl. No. 14/550,573.
U.S. Appl. No. 12/741,995 (Publication No. US 2012-0018531 A1) Now U.S. Pat. No. 9,089,724 issued Jul. 28, 2015; Related Application to U.S. Appl. No. 14/550,573.
U.S. Appl. No. 14/806,160 (Publication No. US 2016-0038954 A1) Related Application to U.S. Appl. No. 14/550,573.
U.S. Appl. No. 14/086,680 (Publication No. US 2014-0076996 A1) Related Application to U.S. Appl. No. 14/550,573.
U.S. Appl. No. 14/519,488 (Publication No. US 2015-0048176 A1) Related Application to U.S. Appl. No. 14/550,573.
U.S. Appl. No. 14/895,649 (Publication No. US 2016-0136672 A1) Related Application to U.S. Appl. No. 14/550,573.
U.S. Appl. No. 14/775,975 (Publication No. US 2016-0030958 A1) Related Application to U.S. Appl. No. 14/550,573.

* cited by examiner

MIST GENERATING APPARATUS

This application is a continuation application of U.S. patent application Ser. No. 14/342,777, filed. Mar. 4, 2014 which is a 35 U.S.C. § 371 application of International Application No. PCT/GB2012/052108 filed Aug. 28, 2012, which claims the benefit of priority to Great Britain Patent Application No. 1115412.7, filed Sep. 7, 2011, each of which is incorporated by reference in its entirety.

The present invention relates to the field of mist generation, and more particularly to an improved twin-fluid mist generating apparatus capable of spraying mists over a spray angle of 360 degrees about the apparatus. The present invention is particularly suited to applications in the fields of fire suppression, decontamination, disinfection, dust suppression, particle tie-down and cooling.

Twin-fluid mist generating apparatus generate a spray mist by the interaction of a first driving fluid with a second process fluid. Such apparatus which can spray mists over a spray angle of substantially 360 degrees are known. These apparatus utilise a nozzle which extends around the entire circumference of the apparatus and which is at substantially 90 degrees to the longitudinal axis of the apparatus. As a result, in normal operation (where the apparatus is mounted on a horizontal surface such as a floor or ceiling) the apparatus will spray a mist over a 360 spray angle, with the mist exiting the nozzle substantially parallel to the surface upon which the apparatus is mounted.

In certain applications the location of the mist generating apparatus in a room or enclosed space is dictated by operating requirements of that room or space. For example, in decontamination applications targeting insects, spores or fungi in warehouses storing perishable goods it is usually necessary to place the mist generating apparatus as close to the ceiling of the room as possible, or locate the apparatus in a ceiling recess, so that the apparatus does not interfere with the movement of goods, vehicles or cranes within the room. Similarly, in decontamination and fire suppression applications in hospitals and other public buildings the apparatus is preferably placed as close to the ceiling of a room as possible, so that it cannot easily be interfered with or itself interfere with the movement of people and equipment within the room. Additionally, in fire suppression or protection of enclosed spaces it is usually necessary to place the mist generating apparatus as close to the ceiling of the space as possible, or else locate the apparatus in a recess in the ceiling, so that the apparatus does not interfere with the movement of goods, vehicles or equipment within the space. Positioning the mist generating apparatus in this way can limit the performance of the apparatus, as if the apparatus is too close to the mounting surface spray droplets issuing substantially parallel to the surface are likely to be attracted towards, and possibly land upon, the mounting surface rather than continuing into the volume being filled with mist. The droplets then coalesce on the surface, creating larger droplets which eventually drop off the surface rather than reaching the extremities of the volume. The problems can be even more pronounced when the apparatus is recessed, with the majority of the spray droplets simply coalescing on the surfaces of the recess rather than travelling out into the space. Thus, the ability of the mist generating apparatus to spray a mist into the furthest reaches of an enclosed space can be restricted when the apparatus is mounted close to a surface or within a recess.

It is an aim of the present invention to obviate or mitigate these disadvantages of this type of mist generating apparatus.

According to a first aspect of the present invention, there is provided a mist generating apparatus having a longitudinal axis and comprising:

first and second opposing nozzle surfaces which define a nozzle therebetween; and a first process fluid passage having an inlet connectable to a supply of process fluid, and a process fluid outlet on one of the first and second nozzle surfaces such that the process fluid outlet opens into the nozzle;

wherein the nozzle has a nozzle inlet connectable to a supply of driving fluid, a nozzle outlet, and a throat portion intermediate the nozzle inlet and nozzle outlet, wherein the nozzle throat has a cross sectional area which is less than that of both the nozzle inlet and the nozzle outlet;

wherein the nozzle extends radially away from the longitudinal axis such that the nozzle defines a rotational angle about the longitudinal axis; and wherein a centre line of the nozzle extending from the nozzle throat to the nozzle outlet is at an angle of between 50 and 80 degrees relative to the longitudinal axis.

The centre line of the nozzle is a line which divides the nozzle into equal upper and lower parts when the nozzle is viewed in cross section. The centre line extends through points at the nozzle throat and nozzle outlet which are equidistant the surfaces defining the nozzle throat and nozzle outlet, respectively.

References to "radial" and "radially" in this specification are to be understood as "extending or spreading from a centre outwards", the centre in this case being the longitudinal axis of the apparatus. In this specification. "radial" and "radially" do not limit the referenced direction to one which is specifically at right angles to the longitudinal axis.

The nozzle may be symmetrical about the centre line, whereby a line extending perpendicular to the centre line between the nozzle surfaces at any point between the nozzle throat and nozzle outlet inclusive is bisected by the centre line.

The apparatus may further comprise first and second exterior surfaces which adjoin the first and second nozzle surfaces, respectively, at the nozzle outlet, and when viewed in cross section both the first and second exterior surfaces lie at an angle of substantially 90 degrees or less relative to the nozzle centre line. The first and second exterior surfaces may lie at the same angle relative to the nozzle centre line. Alternatively, the first and second exterior surfaces may lie at first and second angles of 90 degrees or less relative to the nozzle centre line.

The nozzle may be asymmetrical about the centre line, whereby a line connecting the first and second nozzle surfaces at the nozzle outlet is divided into two unequal portions by the centre line.

The apparatus may further comprise first and second exterior surfaces which adjoin the first and second nozzle surfaces, respectively, at the nozzle outlet, and when viewed in cross section at least the second exterior surface lies at an angle of 90 degrees or less relative to the nozzle centre line.

The second nozzle surface may include a Coanda surface on a curved or convex lip portion which projects radially outwards of the nozzle outlet.

The nozzle may define a rotational angle of between 15 and 180 degrees about the longitudinal axis. Alternatively, the nozzle may define a rotational angle of 360 degrees about the longitudinal axis.

The nozzle outlet may be continuous around a portion of the perimeter of the apparatus covered by the rotational angle. Alternatively, the nozzle outlet may be discontinuous around a portion of the perimeter of the apparatus covered by the rotational angle. The apparatus may further comprise one or more filler members which may be inserted into the nozzle outlet to create a discontinuity therein.

The first process fluid outlet may open into the nozzle from the first nozzle surface in the nozzle throat or at a point downstream thereof. The process fluid outlet may be annular and extend circumferentially about the longitudinal axis.

The apparatus may further comprise a second process fluid passage having an inlet connectable to a supply of process fluid, and an outlet on the second nozzle surface, the outlet opening into the nozzle intermediate the nozzle throat and the nozzle outlet.

According to a second aspect of the present invention, there is provided a mist generating apparatus having a longitudinal axis and comprising:
   first and second opposing nozzle surfaces which define a nozzle therebetween; and
   a first process fluid passage having an inlet connectable to a supply of process fluid, and a process fluid outlet on one of the first and second nozzle surfaces such that the process fluid outlet opens into the nozzle;
   wherein the nozzle has a nozzle inlet connectable to a supply of driving fluid, a nozzle outlet, and a throat portion intermediate the nozzle inlet and nozzle outlet, wherein the nozzle throat has a cross sectional area which is less than that of either the nozzle inlet or the nozzle outlet;
   wherein the nozzle extends radially away from the longitudinal axis such that the nozzle defines a rotational angle about the longitudinal axis; and
   wherein the second nozzle surface includes a Coanda surface on a lip portion which projects radially outwards of the nozzle outlet.

The nozzle may define a rotational angle of between 15 and 180 degrees about the longitudinal axis. Alternatively, the nozzle may define a rotational angle of 360 degrees about the longitudinal axis.

The nozzle outlet may be continuous around a portion of the perimeter of the apparatus covered by the rotational angle. Alternatively, the nozzle outlet may be discontinuous around a portion of the perimeter of the apparatus covered by the rotational angle. The apparatus may further comprise one or more filler members which may be inserted into the nozzle outlet to create a discontinuity therein.

The first process fluid outlet may open into the nozzle from the first nozzle surface in the nozzle throat or at a point downstream thereof. The process fluid outlet may be annular and extend circumferentially about the longitudinal axis.

The apparatus may further comprise a second process fluid passage having an inlet connectable to a supply of process fluid, and an outlet on the second nozzle surface, the outlet opening into the nozzle intermediate the nozzle throat and the nozzle outlet.

According to a third aspect of the invention, there is provided a method of generating a mist with a mist generating apparatus having a longitudinal axis, the method comprising:
   supplying a flow of driving fluid to a nozzle extending radially away from the longitudinal axis such that the nozzle defines a rotational angle about the longitudinal axis, the nozzle defined between first and second opposing nozzle surfaces of the apparatus and comprising a nozzle inlet, a nozzle outlet, and a nozzle throat intermediate the nozzle inlet and nozzle outlet, and the nozzle throat having a cross sectional area which is less than that of both the nozzle inlet and nozzle outlet, and a centre line extending from the nozzle throat to the nozzle outlet at an angle of between 50 and 80 degrees relative to the longitudinal axis;
   supplying a process fluid from a process fluid outlet on one of the first and second nozzle surfaces to the nozzle in the nozzle throat or at a point downstream thereof;
   accelerating the flow of driving fluid as it passes through the nozzle throat, whereby the accelerated driving fluid atomises the process fluid exiting the process fluid outlet to form a mist comprising a dispersed phase of process fluid droplets in a continuous vapour phase of driving fluid; and
   spraying the mist from the nozzle radially of the longitudinal axis at the angle of between 50 and 80 degrees relative to the longitudinal axis.

The nozzle outlet may be continuous around a portion of the perimeter of the apparatus covered by the rotational angle. Alternatively, the nozzle outlet may be discontinuous around a portion of the perimeter of the apparatus covered by the rotational angle. In the latter case, the method may comprise an initial step of inserting one or more filler members into the nozzle outlet to form discontinuities therein.

According to a fourth aspect of the invention, there is provided a method of generating a mist with a mist generating apparatus having a longitudinal axis, the method comprising:

supplying a flow of driving fluid to a nozzle extending radially away from the longitudinal axis such that the nozzle defines a rotational angle about the longitudinal axis, the nozzle defined between first and second opposing nozzle surfaces of the apparatus and comprising a nozzle inlet, a nozzle outlet, and a nozzle throat intermediate the nozzle inlet and nozzle outlet, and the nozzle throat having a cross sectional area which is less than that of both the nozzle inlet and nozzle outlet, and the second nozzle surface includes a downwardly-curving Coanda surface on a lip portion which projects radially outwards of the nozzle outlet;

supplying a process fluid from a process fluid outlet on one of the first and second nozzle surfaces to the nozzle in the nozzle throat or at a point downstream thereof;

accelerating the flow of driving fluid as it passes through the nozzle throat, whereby the accelerated driving fluid atomises the process fluid exiting the process fluid outlet to form a mist comprising a dispersed phase of process fluid droplets in a continuous vapour phase of driving fluid; and spraying the mist from the nozzle radially of the longitudinal axis towards the Coanda surface such that at least a portion of the mist is directed downwards by the Coanda surface.

The nozzle outlet may be continuous around a portion of the perimeter of the apparatus covered by the rotational angle. Alternatively, the nozzle outlet may be discontinuous around a portion of the perimeter of the apparatus covered by the rotational. In the latter case, the method may comprise an initial step of inserting one or more filler members into the nozzle outlet to form discontinuities therein.

Preferred embodiments of the present invention will now be described, by way of example only, with reference to the accompanying drawings in which:

FIG. 1 is a cross section through a first embodiment of a mist generating apparatus;

FIG. 2 is a cross section through the spray head of the apparatus shown in FIG. 1;

Figure 1:
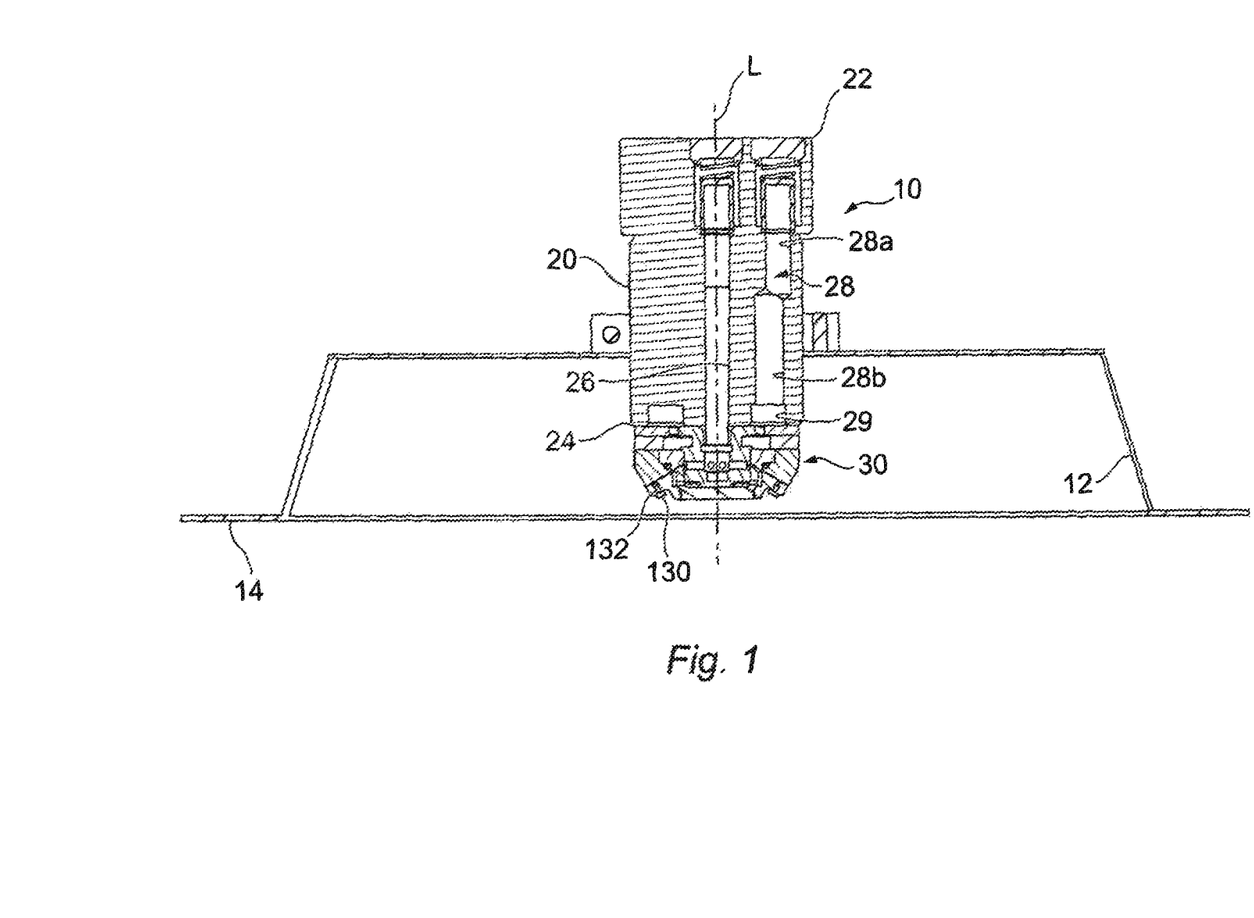

FIG. 1 shows a first embodiment of a mist generating apparatus, generally designated 10. In the illustrated embodiment the apparatus 10 is housed within a recess 12 in the upper surface 14 of the volume into which the apparatus is to spray a mist. This volume may be in, for example, a warehouse, operating theatre, mass transit system vehicle, or the cargo hold of an aircraft. In these and other applications the apparatus 10 may be utilised as part of a fire suppression system, with the apparatus 10 recessed so that personnel, equipment, stored goods and the like do not come into contact with the apparatus 10. However, it should be understood that the present invention is not limited to recessed applications alone, as will be discussed below.

The apparatus 10 comprises a substantially cylindrical body 20 having a first end 22 located above the recess 12 for connection to fluid supply lines (not shown), and a second end 24 projecting into the recess 12. The apparatus 10 further comprises a spray head 30 which is attached to the second end 24 of the body 20. Two fluid passages 26,28 are defined within the body 20. The first passage 26 is co-axial with a longitudinal axis L of the apparatus 10 and supplies a driving fluid from a driving fluid supply (not shown) to the spray head 30. The second passage 28 is radially offset from the longitudinal axis L but is substantially parallel thereto. The second passage 28 supplies a process fluid from a process fluid supply (not shown) to the spray head 30. The second passage 28 preferably comprises an upstream section 28a and a downstream section 28b. Both sections 28a,28b of the second passage 28 are substantially parallel to the longitudinal axis L but the downstream section 28b is radially inward of the upstream section 28a such that an offset exists in the radial direction between the two sections 28a,28b of the second passage 28. The second passage 28 opens into an annular channel at the second end 24 of the body 20. With the spray head 30 attached as shown in FIG. 1, the annular channel becomes an annular chamber 29.

Figure 2:
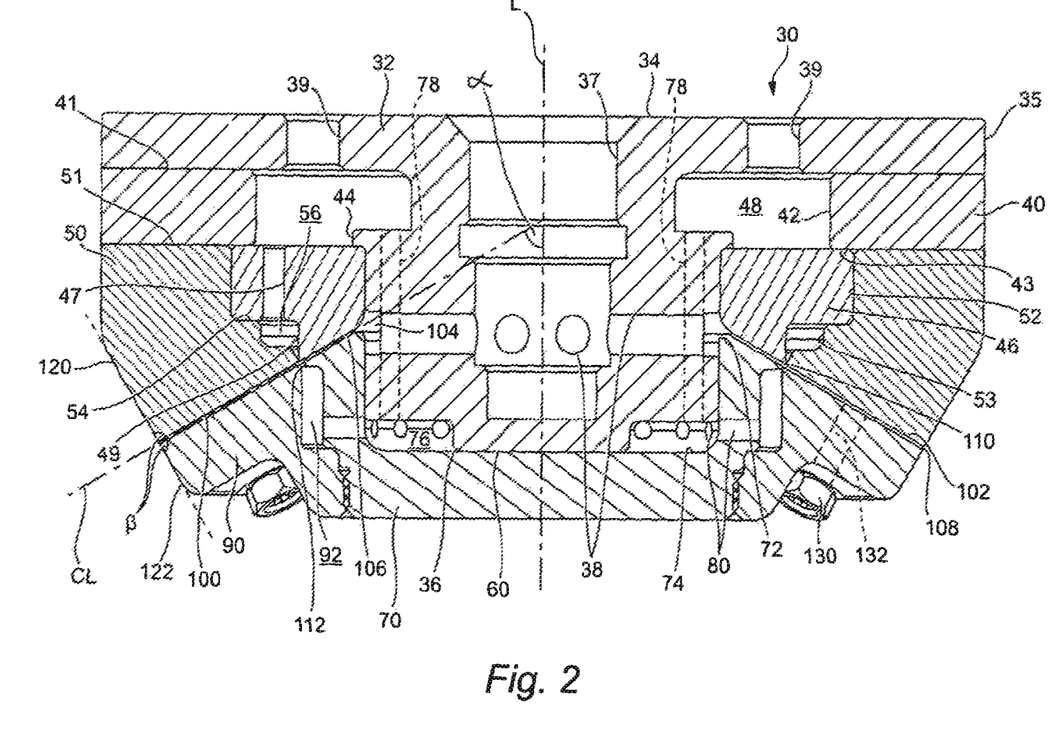
Figure 3:
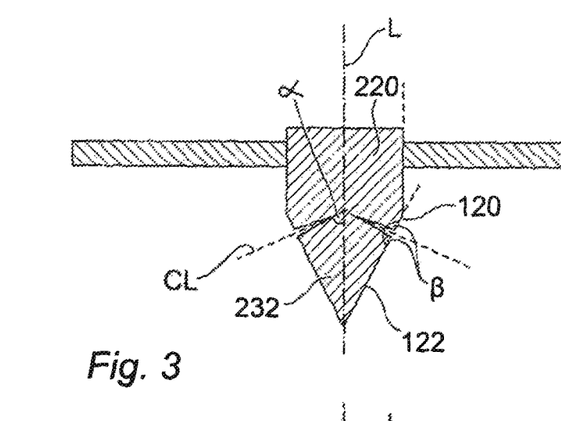
FIGS. 3-6 are schematic cross sections through alternative embodiments of the mist generating apparatus.
Figure 4:
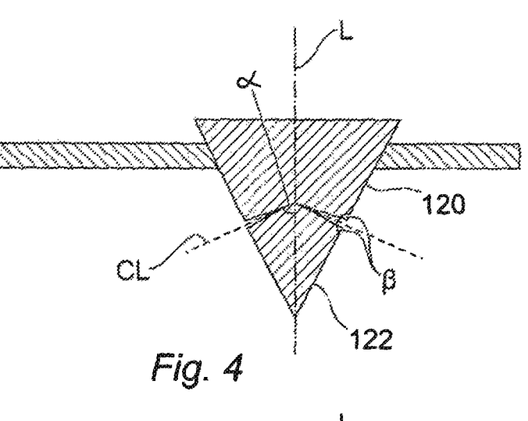
Figure 5:
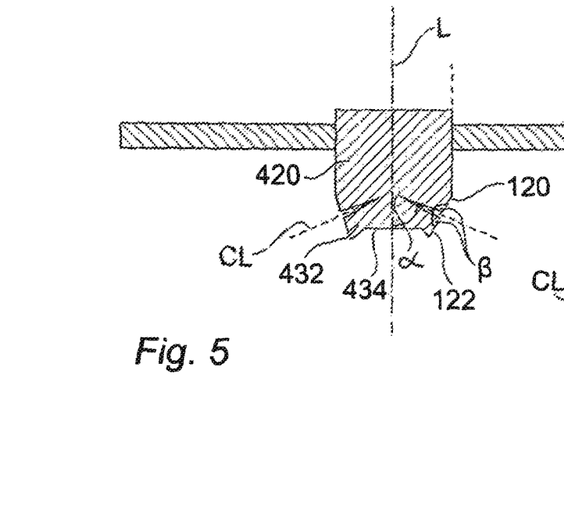
Figure 6:
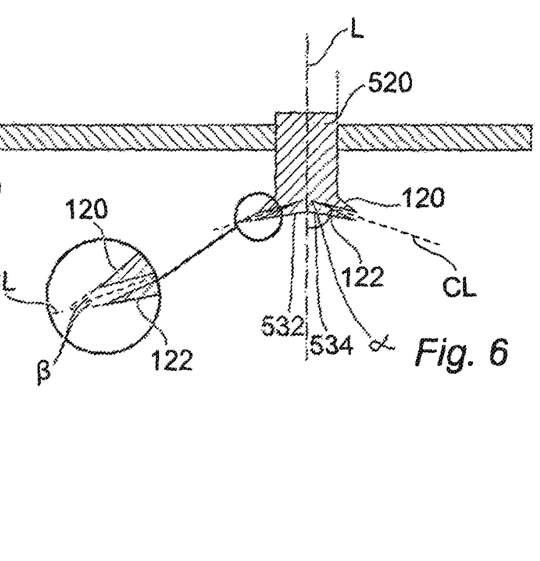
Figure 7:
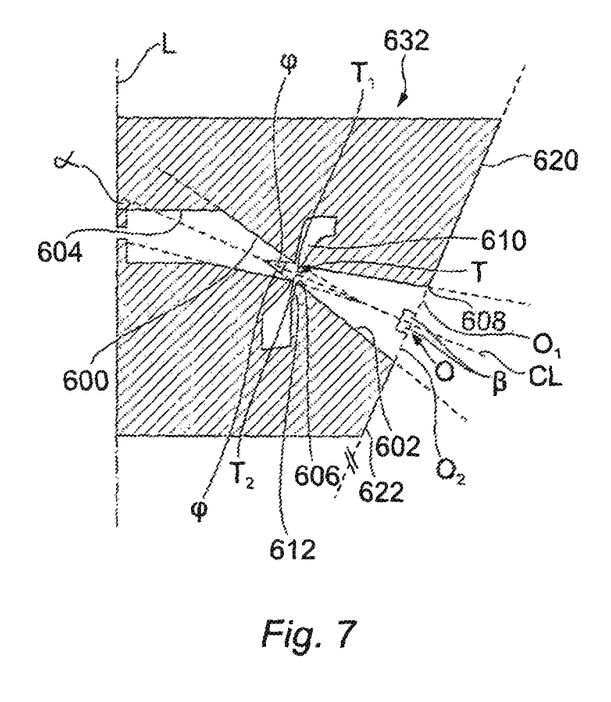
FIGS. 7-11 are schematic cross sections of alternative embodiments of nozzle for use in the mist generating apparatus.

The spray head 30 is shown in more detail in FIG. 2. The spray head 30 comprises a generally cylindrical spray member 32 having a first end 34 and a second end 36. The first end 34 includes a radially extending flange 35 and is adapted to be attached to the second end 24 of the body 20, as shown in FIG. 1. The spray member includes a blind bore 37 which is co-axial with the longitudinal axis L shared by the apparatus 10 and spray head 30. As shown in FIG. 1, the bore 37 connects with the first passage 26 so as to receive driving fluid from the first passage 26. Extending radially outwards from the bore 37 are a number of nozzle supply passages 38.

The flange 35 includes a plurality of passages 39 circumferentially spaced about the longitudinal axis L, which in use allow the annular chamber 29 in the body 20 to communicate with the spray head 30. An annular spacer 40 has a first side 41 which abuts the flange 30 such that an annular space is defined between an inner surface 42 of the first spacer 40 and the spray member 32. The spray member 32 includes a radially-projecting lip 44, and an annular inner insert 46 is brought into abutment with the lip 44 and a second side 43 of the spacer 40, whereby an annular first process fluid chamber 48 is defined between the spray member 32, the first spacer 40 and the inner insert 46. The inner insert 46 includes a longitudinal passage 47, which allows fluid communication between upstream and downstream sides of the inner insert 46, and hence downstream from the first process fluid chamber 48.

An annular outer insert 50 as a first side 51 which abuts the second side 43 of the spacer 40, and an internal surface having a first portion 52 whose internal diameter is greater than that of a second portion 53. The difference in internal diameter between the first and second portions 52,53 of the outer insert 50 forms a locking surface 54, which in use engages the downstream side of the inner insert 46 in order to secure the inner insert 46 in position against the spacer 40 and lip 44 of the spray member 32. A second process fluid chamber 56 is defined between the second portion 53 of the outer insert 50 and an outer surface 49 of the insert 46, whereby the passage 47 in the inner insert 46 opens into the second process fluid chamber 56.

The second end 36 of the spray member 32 includes an axial projection 60. A cup member 70 has an open first end 72 and a closed second end 74. The cup member 70 defines an internal space whose internal diameter is substantially the same as the external diameter of the second end 36 of the spray member 32. Consequently, the cup member 70 fits over the second end 36 of the spray member 32 such that the closed end 74 of the cup 70 abuts the axial projection 60. As a result, a third annular process fluid chamber 76 is defined between the cup member 70 and the second end 36 of the spray member 32. A plurality of axially extending passages 78 in the spray member 32 permit fluid communication between the first and third process fluid chambers 48,76. The cup member 70 also includes a number of circumferentially-spaced passages 80, which permit fluid flow from the interior to the exterior of the cup member 70, and hence outwardly from the third process fluid chamber 76.

Finally, an annular cap 90 is fitted over the exterior of the cup 70 with at least a portion of the inner diameter of the cap 90 being greater than the outer diameter of the cup 70, such that a fourth process fluid chamber 92 is defined between the cap 90 and cup 70 at the location where the cup passages 80 open on the exterior of the cup 70.

It should be noted that a number of functional components have been omitted from the drawings for illustrative purposes. Specifically, where appropriate the various components would include circumferential grooves and O-ring seals located in those grooves so as to provide fluid seals between each of the components and also to ensure that the apparatus as a whole is airtight. Additionally, a plurality of known mechanical fixtures such as, for example, screws, nuts and bolts are not shown but would be incorporated into the apparatus so as to secure the components in the positions shown in the figures.

As can be seen in FIG. 2, the cup 70 and cap 90 do not abut the inner and outer inserts 46,50. Instead, the engagement of the second end 74 of the cup 70 with the axial projection 60 on the spray member 32 ensures that a gap is present between the first end 72 of the cup 70 and the inner insert 46. Similarly, the inner surface of the cap 90 and outer surface of the cup 70 engage in such a way that the surface of the cap 90 adjacent the outer insert 50 provides a gap between those two components. It is the inner and outer inserts 46,50, the cup 70, cap 90 and gaps therebetween which define the nozzle of the spray head 32. The lower surfaces of the inner and outer inserts 46,50 collectively provide a first nozzle surface 100, which opposes a second nozzle surface 102 collectively provided by the upper surface of the cap 90 and the first end 72 of the cup 70 on the other side of the gap. A nozzle inlet 104 is defined between the inner insert 46 and first end 72 of the cup 70, and is in fluid communication with the nozzle supply passages 38. A nozzle outlet 108 is defined between the outer insert 50 and cap 90. The nozzle also includes a throat portion 106 intermediate the nozzle inlet 104 and nozzle outlet 108, the nozzle throat 106 having a cross sectional area which is less than that of both the nozzle inlet 104 and nozzle outlet 108. In this preferred embodiment, the reduction in cross sectional area from the nozzle inlet 104 to the throat 106 is achieved by the narrowing of the gap in the radial direction between the inner insert 46 and first end 72 of the cup 70. Whilst the gap then remains substantially constant from the nozzle throat 106 to the nozzle outlet 108, the cross sectional area at the outlet 108 is greater than at the throat due to the 360 degree rotational angle of the nozzle about the longitudinal axis L of the apparatus and the fact that the outlet 108 is at a greater distance than the nozzle throat 106 from the longitudinal axis L in a direction perpendicular to the longitudinal axis L.

A nozzle adjustment mechanism may also be incorporated in the apparatus. As best seen in FIG. 1, the adjustment mechanism may comprise a number of threaded adjusters 130 which are received within threaded apertures 132 extending through the cap 90 so that an inner end of each adjuster 130 lies against the first nozzle surface 100 on the outer insert 50. An outer end of each adjuster 130 lies proud of the cap 90 so that it may be rotated clockwise or counter-clockwise. Rotation of the adjusters 130 clockwise will push the cap 90 and cup 70 attached thereto away from the inner and outer inserts 46, 50, whilst counter-clockwise rotation will result in the cap 90 and cup 70 moving closer to the inner and outer inserts 46,50. In this way, the nozzle adjustment mechanism can adjust the distance between the first and second nozzle surfaces 100,102 and thus vary the velocity and/or flow rate of the driving fluid and the resultant degree of atomisation of the process fluid.

A small gap also exists between the inner and outer inserts 46,50, which acts as a first process fluid outlet 110 allowing fluid communication between the second process fluid chamber 56 and the nozzle. A similar arrangement exists between the cup 70 and cap 90, wherein the gap between those two components acts as a second process fluid outlet 112 allowing fluid communication between the fourth process fluid chamber 92 and the nozzle. The nozzle has a centre line CL which when the nozzle is viewed in cross section extends through first and second points in the nozzle throat 106 and nozzle outlet 108, respectively, where those first and second points are the midpoints between the first and second surfaces at the nozzle throat 106 and nozzle outlet 108, respectively. The centre line lies at an angle α of between 50 and 80 degrees relative to the longitudinal axis L.

The outer insert 50 and cap 90 have respective first and second exterior surfaces 120,122 which adjoin the first and second nozzle surfaces 100,102, respectively, at the nozzle outlet 108. When viewed in cross section in the manner shown in both FIGS. 1 and 2, both the first and second exterior surfaces 120,122 lie at an angle β of substantially 90 degrees or less relative to the nozzle centre line CL.

The manner in which the apparatus shown in FIGS. 1 and 2 operates will now be described. Initially, a first pressurised supply of process fluid (not shown) is connected to the inlet of the second passage 28. The process fluid in this example is water. The process fluid passes from the passage 28 into the annular chamber 29, and from there into the first process fluid chamber 48 via the passages 39. From there, the process fluid exits the first process fluid chamber 48 via the passage 47 and enters the second process fluid chamber 56. The process fluid leaves the second process fluid chamber 56 via the first process fluid outlet 110 defined between the inner and outer inserts 46,50. The first outlet 110 has a smaller cross sectional area than that of the second chamber 56, with the result that the process fluid exits through the outlet 110 as a thin ring of process fluid.

At the same time as the process fluid passes from the first to the second process fluid chambers 48,56 via the passage 47, a portion of the process fluid is also passing from the first process fluid chamber 48 to the third process fluid chamber 76 via the passages 78. From there, the process fluid flows into the fourth process fluid chamber 92 via the passages 80 provided in the cup 70. The process fluid leaves the fourth process fluid chamber 92 via the second process fluid outlet 112 defined between the cup 70 and cap 90. The second outlet 112 has a smaller cross sectional area than that of the fourth chamber 92, with the result that the process fluid exits through the outlet 112 as a thin ring of process fluid. Thus, both streams of process fluid enter the nozzle from their respective outlets 110,112 as thin annuli of process fluid.

As the process fluid enters the apparatus 10, so does a supply of driving fluid. The driving fluid, preferably nitrogen, enters the first passage 26 in the body 20. Consequently, driving fluid enters the blind bore 37 in the spray member 32, and from there it passes through each of the nozzle supply passages 38 into the nozzle inlet 104 defined between the inner surfaces of the inner insert 46 and cup 70.

The preferred supply pressures of the driving and process fluids, as well as the preferred mass flow ratios between the two fluid supplies, are dependent on the particular application for which the apparatus is to be used. For example, in a decontamination application the mass flow ratio between the process fluid and driving fluid is preferably between 1:1 and 2:1. In other words, in the preferred range the mass flow ratio would be 1-2 kg of process fluid for every 1 kg of driving fluid. In this application the preferred supply pressure ranges are 2-4 bar (gauge) for the process fluid and 3.5-4.5 bar (gauge) for the driving fluid. In a fire suppression application the mass flow ratio between the two fluids is between 3:1 and 8:1, with 3-8 kg of process fluid for every 1 kg of driving fluid. The supply pressure ranges for a fire suppression application are preferably 440 bar (gauge) for the process fluid and 5-12 bar (gauge) for the driving fluid.

The total cross sectional area of the nozzle supply passages 38 is greater than that of the nozzle throat 106 defined between the inner insert 46 and cup 70. As the nozzle extends in the radial direction towards the nozzle outlet 108, its cross sectional area increases again. As the driving fluid enters the nozzle the reduced cross sectional area of the nozzle throat 106 causes the driving fluid to undergo a significant acceleration. This acceleration causes the velocity of the driving fluid to significantly increase, preferably to at least sonic velocity and most preferably to a supersonic velocity depending on the parameters of the driving fluid supplied to the apparatus. The driving fluid then comes into contact with the twin streams of process fluid exiting the first and second outlets 110,112.

As the driving and process fluids come into contact with one another an energy transfer takes place, primarily as a result of mass and momentum transfer between the high velocity driving fluid and the relatively low velocity process fluid. This energy transfer imparts a shearing force on the process fluid streams, leading to the atomisation of the process fluid. This atomisation leads to the formation of a mist made up of a dispersed phase of process fluid droplets in a continuous vapour phase of driving fluid. The mist sprays from the apparatus 10 at the angle α relative to the longitudinal axis L, and over a preferred rotational spray angle about the axis L of substantially 360 degrees. With the exterior surfaces 120,122 lying at the angle β of substantially 90 degrees or less relative to the centre line CL of the nozzle, the mist droplets spraying from the nozzle outlet 108 are not subject to any Coanda effects which would attract them to those exterior surfaces 120,122.

Figure 8:
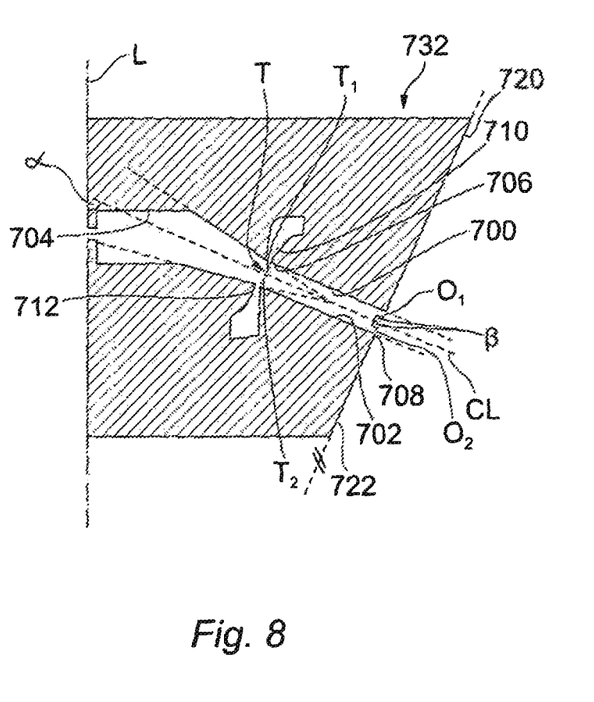

FIGS. 3 to 6 show schematic cross sections of alternative embodiments of the mist generating apparatus. These alternative embodiments are similar to the first embodiment shown in FIGS. 1 and 2, in that they each employ a nozzle whose centre line CL, when viewed in cross section, is at the angle α of between 50 and 80 degrees relative to the longitudinal axis L of the apparatus, and each has first and second exterior surfaces 120,122 which—when also viewed in cross section as per these FIGS. 3 to 6—lie at the angle β of substantially 90 degrees or less relative to the centre line CL. Where these embodiments differ from each other and the first embodiment is in their overall shape. The second embodiment shown in FIG. 3 combines a generally cylindrical body 220 with a conical spray head 230. FIG. 4 illustrates a third embodiment in which the entire apparatus is conical, rather than just the spray head. FIG. 5 illustrates a fourth embodiment similar to the first embodiment, in which the body 420 is generally cylindrical and the spray head 430 is frustoconical. However, in the fourth embodiment an end 434 of the spray head 430 remote from the body 420 is concave. FIG. 6 illustrates a fifth embodiment in which the spray head 530 has a larger diameter than that of the generally cylindrical body 520, as well as having an end 534 remote from the body 520 which is concave. As the spray head 530 has a concave end 534 and a larger diameter than the body 520, the angles β at which the first and second exterior surfaces 120,122 lie relative to the nozzle centre line CL are much shallower in the fifth embodiment, creating a pair of "knife edges" at the nozzle outlet 508.

FIGS. 7 to 11 show schematic cross sections of various embodiments of nozzle which may form part of the present invention. Only one half of each nozzle cross section is shown for illustrative purposes, with it being understood that the other half of the nozzle would be a mirror image of the half shown, about the longitudinal axis L. Each nozzle employed in the present invention is a convergent-divergent nozzle. This term is to be understood as referring to a nozzle whose cross sectional area reduces from nozzle inlet to a nozzle throat, and then increases again from the nozzle throat to nozzle outlet. These changes in cross sectional area are linear, or at least gradual, such that the surfaces defining the nozzle are smooth and free from any steps or protrusions caused by sudden increases or decreases in cross sectional area within the nozzle. As with the nozzle described above, each of these nozzles has a centre line CL which in cross section lies at an angle α of between 50 and 80 degrees relative to the longitudinal axis L. Furthermore, these nozzles themselves generate a mist in the same manner as described above with respect to the first embodiment of the mist generating apparatus.

FIG. 7 shows a first embodiment of spray head 630 having a nozzle defined by first and second opposing nozzle surfaces 600,602. The nozzle has a nozzle inlet 604 connected to a driving fluid supply (not shown), a nozzle outlet 608, and a nozzle throat 606 intermediate the nozzle inlet 604 and nozzle outlet 608. The throat 606 has a cross sectional area which is less than that of the inlet 604 and outlet 608. In this embodiment, the nozzle surfaces 600,602 downstream of the nozzle throat lie at an angle φ relative to the nozzle centre line CL when viewed in cross section. In the same view the exterior surfaces 620,622 of the spray head 630 lie at an angle β of substantially 90 degrees relative to the nozzle centre line CL. The nozzle includes at least one process fluid outlet 610 on the first nozzle surface 600. Preferably, there is also a process fluid outlet 612 on the second nozzle surface 602. The outlets 610,612 open into the nozzle in the nozzle throat 606 or downstream thereof.

FIG. 8 shows a second embodiment of spray head 730, which employs a nozzle identical to that used in the first embodiment of the apparatus and shown in detail in FIG. 2. This second embodiment is included here so as to more clearly show the relationships between the various surfaces of the nozzle and spray head. The nozzle is defined by first and second opposing nozzle surfaces 700,702. The nozzle has a nozzle inlet 704 connected to a driving fluid supply (not shown), a nozzle outlet 708, and a nozzle throat 706 intermediate the nozzle inlet 704 and nozzle outlet 708. The throat 706 has a cross sectional area which is less than that of the inlet 704 and outlet 708. In this embodiment, the nozzle surfaces 700,702 downstream of the nozzle throat 706 lie substantially parallel to the nozzle centre line CL. Although the nozzle surfaces 700,702 do not diverge from one another downstream of the nozzle throat 706, the nozzle is still a convergent divergent nozzle whose cross sectional area at the outlet 708 is greater than that of the throat 706. This is because the nozzle covers a 360 degree rotational angle about the longitudinal axis L and the nozzle outlet 708 is at a greater distance than the nozzle throat 106 from the longitudinal axis L in a direction perpendicular to the longitudinal axis L, so the nozzle outlet 708 has a greater circumference than the nozzle throat 706, and hence a larger cross sectional area despite the nozzle surfaces 700,702 maintaining a constant gap from the nozzle throat 706 to the nozzle outlet 708.

When viewed in cross section as in FIG. 8, the exterior surfaces 720,722 of the spray head 732 lie at an angle β of substantially 90 degrees relative to the nozzle centre line CL. The nozzle includes at least one process fluid outlet 710 on the first nozzle surface 700. Preferably, there is also a process fluid outlet 712 on the second nozzle surface 702. The outlets 710,712 open into the nozzle in the nozzle throat 706 or downstream thereof.

Each of the preceding embodiments utilises a nozzle which is symmetrical about the nozzle centre line. A symmetrical nozzle is one in which a line extending perpendicular to the centre line across the nozzle between the opposing nozzle surfaces at any point between the nozzle throat and nozzle outlet inclusive is bisected by the centre line. Referring specifically to FIGS. 7 and 8, lines T and O can be seen extending perpendicular to the centre line CL across the nozzle at the nozzle throat 606,706 and nozzle outlet 608,708, respectively. Each line T,O is divided into two equal length parts T1,T2,O1,O2 by the centre line CL.

FIG. 9 shows a third embodiment of spray head 830 having a nozzle defined by first and second opposing nozzle surfaces 800,802. The third embodiment of nozzle is similar to the first embodiment shown in FIG. 7, but in the third embodiment a line X connecting the first and second nozzle surfaces 800, 802 across the nozzle outlet 808 is divided into two unequal length portions X1,X2 by the centre line CL. This means that the third embodiment of nozzle is asymmetrical about the nozzle centre line CL, rather than symmetrical in the manner of the previous embodiments. When viewed in cross section as in FIG. 8, the second exterior surface 822 of the spray head 832 lies at an angle β of less than 90 degrees relative to the nozzle centre line CL. The increased length of the first nozzle surface 800 creates a radial lip 821, which in conjunction with the second exterior surface 822 ensures that the ensuing mist sprays outwards and downwards.

Figure 9:
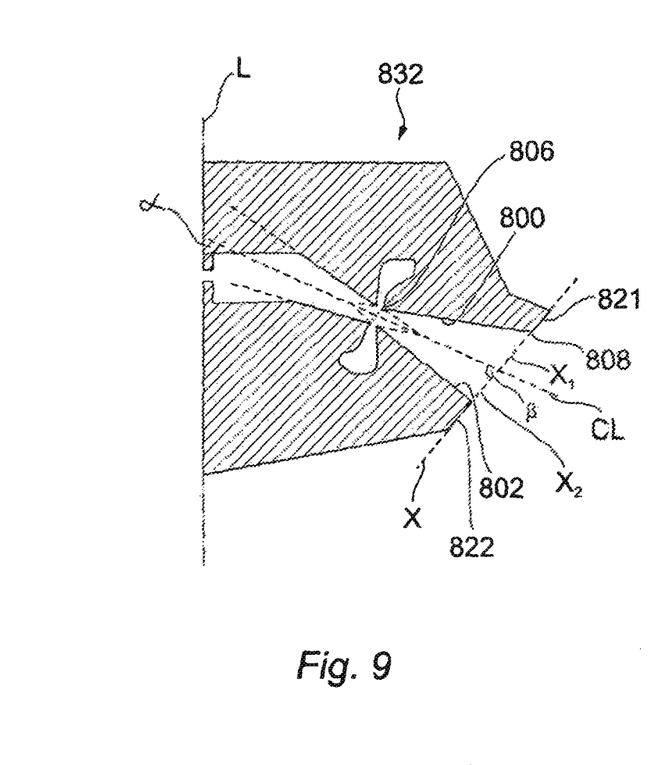
Figure 10:
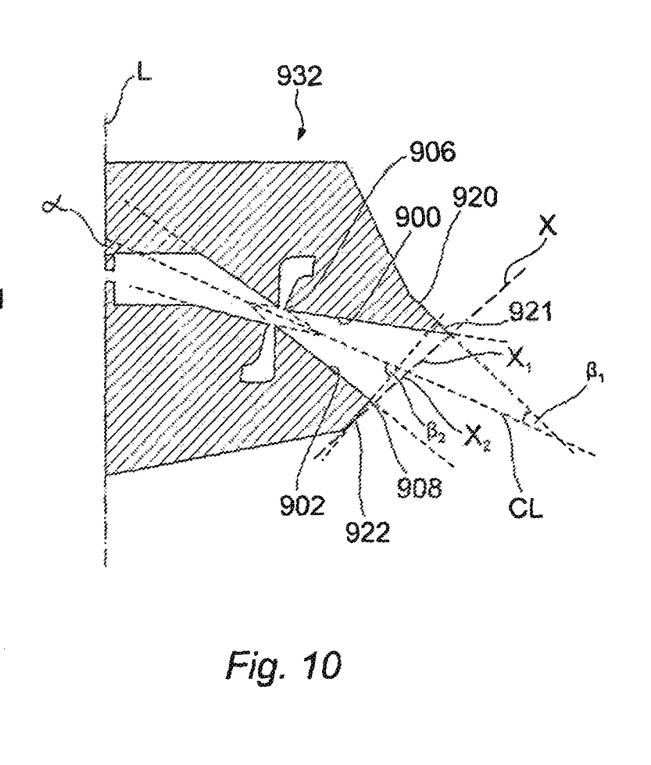

FIG. 10 shows a fourth embodiment of spray head 930 having a nozzle defined by first and second opposing nozzle surfaces 900,902. The fourth embodiment of nozzle is similar to the third embodiment of FIG. 9, in that a line X connecting the first and second nozzle surfaces 900, 902 across the nozzle outlet 908 is divided into two unequal length portions X1,X2 by the centre line CL. This means that like the third embodiment the fourth embodiment of nozzle is also asymmetrical about the nozzle centre line CL. The increased length of the first nozzle surface 900 also creates a radial lip 921, which has a first exterior surface 920. Both the first exterior surface 920, and the second exterior surface 922 which adjoins the second nozzle surface 902, lie at respective angles β1,β2 of less than 90 degrees relative to the nozzle centre line CL, when viewed in cross section as here in FIG. 10.

Figure 11:
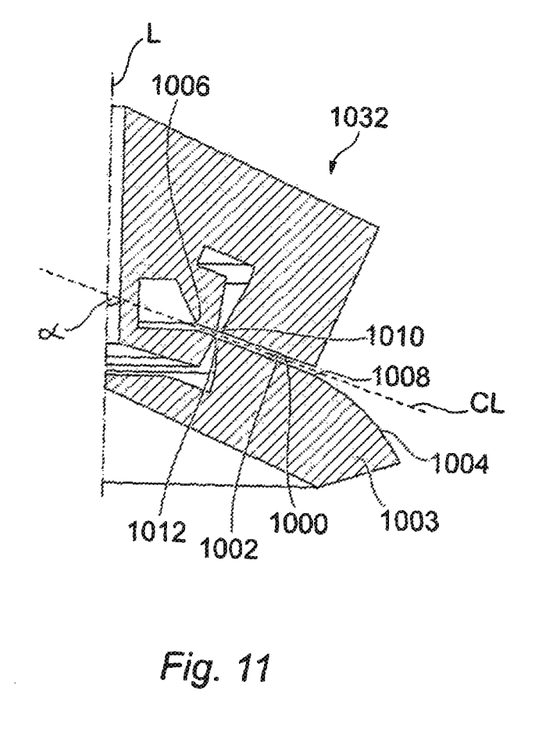
Figure 12:
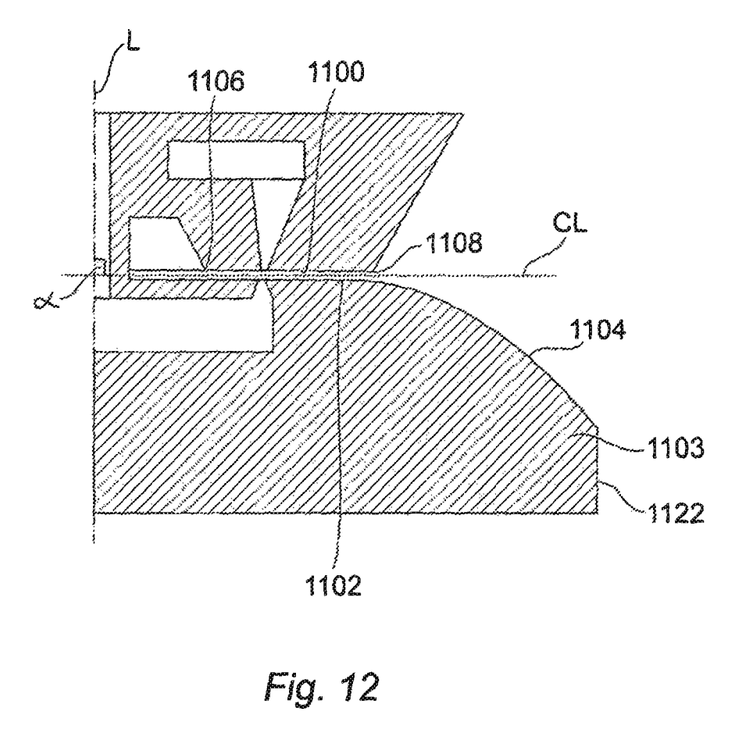
FIG. 12 is a schematic cross section of a further alternative embodiment of nozzle for use in a mist generating apparatus.
Figure 13:
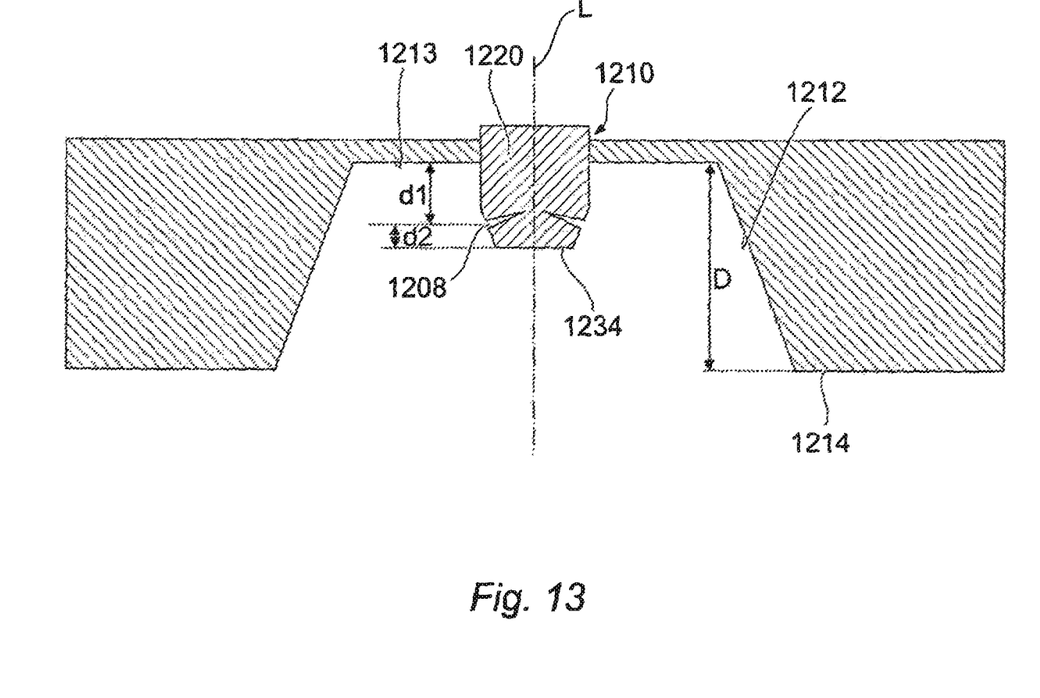
FIG. 13 is a schematic cross section showing a mist generating apparatus located within a recess.

FIG. 11 shows a fifth embodiment of spray head 1030 having a nozzle which is defined by first and second opposing nozzle surfaces 1000,1002. The nozzle is similar to the second embodiment shown in FIG. 8, in that the nozzle surfaces 1000,1002 downstream of the nozzle throat 1006 lie substantially parallel to the nozzle centre line CL when viewed in cross section. Where this embodiment differs from the second embodiment is that the second nozzle surface 1002 includes a lip portion 1003 which projects radially outwards from the nozzle outlet 1008. The lip portion 1003 has a curved Coanda surface 1004 which creates a Coanda effect on the mist issuing from the outlet 1008, encouraging the mist to follow the surface of the lip 1003 in an outward and downward direction. In this embodiment, the first and second process fluid outlets 1010,1012 enter the nozzle downstream of the nozzle throat 1006.

The apparatus and nozzle of the present invention can spray a mist of droplets over a rotational angle of up to 360 degrees about the longitudinal axis of the apparatus. Furthermore, by providing a nozzle whose centre line is at between 50 and 80 degrees relative to the longitudinal axis when viewed in cross section, the apparatus may continue to quickly fill a volume with mist but prevents the concentration and coalescence of droplets on the surface to which the apparatus is mounted. Similarly, if the apparatus must be mounted in a recess for operational reasons, the angling of the nozzle and its centre line ensures that the mist is not concentrated in the recess and instead enters the volume to be filled. The performance of the apparatus can be further enhanced by ensuring that at least one, if not both, of the exterior apparatus surfaces adjoining the nozzle outlet lies at angle of 90 degrees or less relative to the nozzle centre line when the nozzle is viewed in cross section. This removes the possibility of the mist droplets being attracted to the exterior surfaces of the apparatus instead of travelling out into the volume. An alternative enhancement is to provide the projecting lower lip having the curved Coanda surface so as to attract the droplets to the lip but then direct them downwards into the volume by way of the Coanda effect created by the surface.

FIG. 12 shows a schematic cross section of an alternative embodiment of nozzle, which provides an alternative way in which to ensure that the mist generated by the apparatus is issued in a generally downward direction. As with the embodiments of FIGS. 7 to 11, only one half of the nozzle is shown for illustrative purposes, with it being understood that the other half of the nozzle would be a mirror image of the half shown, about the longitudinal axis L. Furthermore, this nozzle is also a convergent-divergent nozzle of the type described above, and generates a mist in the same manner as described above with respect to the first embodiment of the mist generating apparatus.

Where the alternative nozzle of FIG. 12 differs from the previously described embodiments of nozzle is that the nozzle centre line CL is at an angle α of substantially 90 degrees relative to the longitudinal axis L when viewed in cross section as in FIG. 12. Thus, when the mist generating apparatus is mounted in a substantially vertical orientation the mist spraying from the nozzle will issue in a substantially horizontal direction. The nozzle is defined by first and second opposing nozzle surfaces 1100,1102. The nozzle surfaces 1100,1102 downstream of the nozzle throat 1106 lie substantially parallel to the nozzle centre line CL. The second nozzle surface 1102 includes a lip portion 1103 which projects radially outwards from the nozzle outlet 1108. The lip portion 1103 has a curved Coanda surface 1104 which creates a Coanda effect on the mist issuing from the outlet 1108, encouraging the mist to follow the surface of the lip 1103 in a downward direction. The lip portion 1103 may be modified such that the upper surface 1104 ends in a cutaway section having a sharp edge rather than the arrangement of FIG. 12, where the upper surface 1104 ends with an exterior surface 1122 which is generally at right angles to the centre line CL of the nozzle.

FIG. 13 illustrates schematically how any of the embodiments of mist generating apparatus described herein may be positioned within a recess. The illustrated apparatus 1210 shares many of the components already described above in respect of the other embodiments, and those components will not be described again in detail here. The apparatus 1210 is located within a recess 1212 having a recessed surface 1213. The apparatus 1210 is positioned such that the cylindrical body 1220 is partially located in the recessed surface 1213 and extends out into the recess 1212 from the surface 1213. The apparatus 1210 has a longitudinal axis L and the nozzle outlet 1208 of the apparatus is located a first axial distance d1 from the recessed surface 1213. The free, or exposed, end 1234 of the apparatus 1210 is a second axial distance d2 from the nozzle outlet 1208. The recess 1212 has an overall depth D, which is the distance from the recessed surface 1213 to the plane of the ceiling, or upper surface, 1214 of the volume into which the apparatus is to spray a mist. To ensure the proper positioning of the apparatus, the formula $D \geq d1+d2$ must be adhered to. In this way, the apparatus is "fully recessed", by which it is meant that the exposed end and nozzle of the apparatus are as close to the plane of the upper surface 1214 as possible whilst remaining within the recess and protected.

The recess 1212 may be circular with tapered sides, as shown in FIG. 13. Alternatively, the recess may be square- or rectangular-shaped, with or without tapered sides. Any corners within the recess may have a chamfer or radius of curvature to ensure that each corner has a smooth surface with no sharp angles.

The driving fluid utilised in the present invention is preferably compressed air or nitrogen. Alternatively, the driving fluid may be carbon dioxide or steam. The process fluid is preferably water, but may alternatively be liquid fire suppressant decontaminant, for example.

Although a preferred application for the present invention is as part of a fire suppression system, the present invention is not limited to this particular application. The present invention may also be employed in a decontamination or cooling system, for example.

Whilst the preferred embodiments of the present invention comprise first and second process fluid outlets into the nozzle, the invention is not limited to this arrangement. The invention may instead comprise only a single process fluid outlet on either the first or second nozzle surface.

Whilst the preferred embodiments of the nozzle define a rotational angle of substantially 360 degrees, the nozzle may define a smaller rotational angle as required, for example if the apparatus is deployed in the corner of a volume or room. The nozzle may instead therefore define a rotational angle of between 1 and 360 degrees or, most preferably in this particular deployment, between 15 and 180 degrees about the longitudinal axis. This facilitates the fitment of a nozzle within a confined space such as the corner of a room. In the case of such a "limited angle" nozzle, the rotational angle of the process fluid outlet(s) on one or both nozzle surfaces may be smaller than the overall rotational angle of the nozzle to reduce the possibility of the process fluids coming into contact with the internal nozzle walls which define the outer boundaries of the reduced angle nozzle. This reduces the risk of large process fluid droplets being formed on these walls due to coalescence.

In the preferred embodiments, the nozzle outlet is continuous around the portion of the circumference of the apparatus covered by the rotational angle. However, the nozzle outlet may alternatively be discontinuous around the portion of the circumference of the apparatus covered by the rotational angle. In the latter case, the apparatus may further comprise one or more filler members which may be inserted into the nozzle outlet to create discontinuities in the nozzle outlet. Alternatively, the nozzle could be formed with dividing members or similar integrally formed therein to create the discontinuities in the nozzle outlet. However these discontinuities are created, they result in the nozzle outlet being divided into a number of segments, with each segment covering a particular rotational angle about the longitudinal axis. In this case, the process fluid outlet(s) may also be discontinuous and comprise a number of segments which cover the same rotational angles as the nozzle outlet segments. Alternatively, each process fluid segment may cover a smaller rotational angle than its respective nozzle outlet segment to reduce the possibility of the process fluids coming into contact with the internal nozzle walls which define the outer boundaries of the nozzle outlet segments. This reduces the risk of large process fluid droplets being formed on these walls due to coalescence.

Although the preferred range of angle α between the nozzle centre line and the longitudinal axis of the apparatus is between 50 and 80 degrees, it may be desirable to limit the range of angle α to between 60 and 70 degrees in order to limit the possibility of the droplets issuing from the nozzle being attracted to one another or the surface upon which the device is mounted.

Although preferred that the apparatus is mounted on a substantially horizontal surface, the present invention is not limited to this particular arrangement. Instead, the apparatus could alternatively be mounted on a wall or other substantially vertical surface, or else the apparatus could be mounted in a recess on such a surface.

These and other modifications and improvements may be incorporated without departing from the scope of the present invention.

What is claimed is:

1. A mist generating apparatus having a longitudinal axis and comprising:
    first and second opposing nozzle surfaces which define a nozzle therebetween;
    a first driving fluid passage having an inlet axially positioned at the longitudinal axis of the apparatus and connectable to a supply of driving fluid; and
    a first process fluid passage having an inlet radially offset from the longitudinal axis and connectable to a supply of process fluid, and a process fluid outlet on one of the first and second nozzle surfaces such that the process fluid outlet opens into the nozzle;
    wherein the nozzle has a nozzle inlet in fluid communication with the first driving fluid passage, a nozzle outlet, and a nozzle throat intermediate the nozzle inlet and nozzle outlet, wherein the nozzle inlet is spaced radially outward from the inlet of the first driving fluid passage, wherein the nozzle outlet is spaced radially outward from the inlet of the first process fluid passage and the inlet of the first driving fluid passage, and wherein the nozzle throat has a cross sectional area which is less than that of both the nozzle inlet and the nozzle outlet;
    wherein the process fluid outlet opens in the nozzle from the first nozzle surface in the nozzle throat or at a point downstream thereof;
    wherein the nozzle extends from the nozzle inlet to the nozzle outlet radially away from the longitudinal axis such that the nozzle defines a rotational angle about the longitudinal axis; and
    wherein a centre line of the nozzle extending from the nozzle throat to the nozzle outlet is at an angle of between 50 and 80 degrees relative to the longitudinal axis.

2. The apparatus of claim 1, further comprising first and second exterior surfaces which adjoin the first and second nozzle surfaces, respectively, at the nozzle outlet, and when viewed in cross section both the first and second exterior surfaces lie at an angle of 90 degrees or less relative to the nozzle centre line.

3. The apparatus of claim 2, wherein the first and second exterior surfaces lie at the same angle relative to the nozzle centre line.

4. The apparatus of claim 2, wherein the first and second exterior surfaces lie at first and second angles of 90 degrees or less relative to the nozzle centre line.

5. The apparatus of claim 1, wherein the nozzle is asymmetrical about the centre line, whereby a line connecting the first and second nozzle surfaces at the nozzle outlet is divided into two unequal portions by the centre line.

6. The apparatus of claim 5, further comprising first and second exterior surfaces which adjoin the first and second nozzle surfaces, respectively, at the nozzle outlet, and when viewed in cross section at least the second exterior surface lies at an angle of 90 degrees or less relative to the nozzle centre line.

7. The apparatus of claim 1, wherein the second nozzle surface includes a Coanda surface on a curved or convex lip portion which projects radially outward of the nozzle outlet.

8. The apparatus of claim 1, wherein the nozzle defines a rotational angle of between 15 and 180 degrees about the longitudinal axis.

9. The apparatus of claim 1, wherein the nozzle outlet is continuous around a portion of a perimeter of the apparatus covered by the rotational angle.

10. The apparatus of claim 1, wherein the nozzle outlet is discontinuous around a portion of a perimeter of the apparatus covered by the rotational angle.

11. The apparatus of claim 10, further comprising one or more filler members which are inserted into the nozzle outlet to create a discontinuity therein.

12. The apparatus of claim 1, wherein the process fluid outlet is annular and extends circumferentially about the longitudinal axis.

13. The apparatus of claim 1, further comprising a second process fluid passage having an inlet connectable to a supply of process fluid, and an outlet on the second nozzle surface, the outlet opening into the nozzle intermediate the nozzle throat and the nozzle outlet.

* * * * *